United States Statutory Invention Registration [19]

[11] Reg. Number: H645

Dryden, Jr. [43] Published: Jun. 6, 1989

[54] PROCESS FOR THE CONVERSION OF MALEIC ACID DERIVATIVES TO THEIR CORRESPONDING FUMARIC ISOMERS

[75] Inventor: Hugh L. Dryden, Jr., Deerfield, Ill.

[73] Assignee: The NutraSweet Company, Deerfield, Ill.

[21] Appl. No.: 74,102

[22] Filed: Jul. 16, 1987

[51] Int. Cl.[4] ..... C07C 51/353; C07C 102/00; C07C 103/66

[52] U.S. Cl. ..... 560/41; 56/40; 56/146; 56/141; 56/153; 56/146; 56/153; 56/203; 56/169; 56/170; 56/171; 56/172; 56/193

[58] Field of Search ..... 562/595, 556, 591, 571, 562/445-450, 574, 561, 567-568; 560/40-41, 146-147, 153, 203, 169-170, 171-172, 193; 558/355

[56] References Cited

U.S. PATENT DOCUMENTS 2,208,519 7/1940 Spence et al. ..... 562/591
2,454,387 11/1948 Howland et al. ..... 562/598

FOREIGN PATENT DOCUMENTS 30617 9/1973 Japan ..... 562/591

*Primary Examiner*—John F. Terapane
*Assistant Examiner*—Valerie D. Fee
*Attorney, Agent, or Firm*—Craig M. Bell

[57] ABSTRACT

A process for the isomerization of maleic acid, its monoesters and monoamides in the presence of thiourea in anhydrous conditions at elevated temperature to the corresponding fumaryl forms yields intermediates which are useful in the synthetic pathways of aspartame and other useful polypeptides.

11 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PROCESS FOR THE CONVERSION OF MALEIC ACID DERIVATIVES TO THEIR CORRESPONDING FUMARIC ISOMERS

BACKGROUND OF THE INVENTION

The present invention relates generally to processes for isomerization of maleic acid and monoesters and monoamides thereof to the corresponding fumaryl forms.

These fumaryl monoamides and monoesters may be aminated either enzymatically or through microbial fermentation to yield either aspartame (APM) from fumaryl-phenylalanine methyl ester or aspartyl phenylalanine (AP) from fumaryl-phenylalanine. Monobenzyl fumarate could also then be aminated to yield beta-benzyl aspartate which is a useful intermediate in several synthetic pathways for aspartame, but is difficult to prepare by purely chemical means.

Numerous methods have been disclosed for catalytic inversion of maleic acid to fumaric acid according to the following scheme.

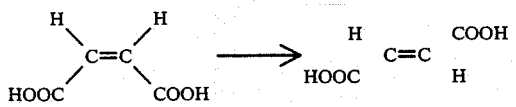

As an early example, Terry and Eichelberger, Journal of the American Chemical Society 47, pp. 1402-1412 (1925) discloses use of hydrobromic acid, hydrochloric acid and potassium thiocyanate catalysts in aqueous solution to isomerize maleic acid to fumaric acid. This procedure, however, has been observed to be without merit as a method of isomerization of maleyl amides and esters due to the fact that amide and ester bonds are easily hydrolyzed under the recommended isomerization conditions. Nozaki and Ogg, J. Am. Chem. Soc. 63, pp 2583–2586 (1941) disclose studies suggesting a mechanism involving both a cation and anion for acid-catalyzed isomerization of maleic acid to fumaric acid in aqueous solution.

Spatz, U.S. Pat. No. 2,548,687 discloses the conversion of maleic acid to fumaric acid catalyzed by mono-, di- and tri-substituted thioureas in heated aqueous solution yielding a 65% recovery of the fumaryl compound. The inventors subsequently disclosed use of this method to isomerize the monomethyl ester of maleic acid to methyl fumarate but note, however, the maleyl monoethyl ester fails to undergo conversion under such conditions. Spatz and Stone, J. Org. Chem. 23, p 1559–1560 (1958).

Thomas. U.S. Pat. No. 3,953,616 discloses a method for preparation of fumarate monoesters from maleate monoesters employing magnesium bromide as a catalyst.

Clemo and Graham, J. Chem. Soc., pp 213–216 (1930), discloses that certain organic bases can serve to assist transformation of methyl maleate to crystalline methyl fumarate. Organic bases noted to be useful for this process include piperidine, dimethylamine, diethylamine, piperazine, methylamine, allylamine, benzylamine, phenylethylamine, and aniline.

Dymicky and Buchanan, Org. Prep. Proc. Intern. 17, No. 2, pp. 121–131 (1985) discloses isomerization of maleyl monoalkyl ester compounds to the corresponding fumaryl monoalkylester compounds. Reaction conditions include elevated temperatures using a fumaryl chloride catalyst to isomerize monoalkyl maleate to monoalkyl fumerate. The alkyl esters contain from one to eighteen single-chained carbon atoms.

British Patent Specification No. 1246349 discloses a method of isomerization of maleyl ester and amide compounds to fumaryl ester and amide compounds in inert aprotic solutions of N,N-dimethyl formamide, hexamethyl phosphoramide, pyridine N-oxide and N,N-dimethyl-O,O'-diethyl phosphoramidate.

German Patent No. DE 3444915-A1 discloses the preparation of fumaryl phenylalanine from maleyl phenylalanine and also describes the use of fumaryl phenylalanine to prepare L-aspartyl L-phenylalanine alkyl esters. No details as to specific methods of preparation are claimed; however, a method is specified as disclosed in the aforementioned British Patent No. 1246349.

Ariyoshi, Japanese Patent No. 74,42,491 discloses synthesis of aspartame in a two step process. Alkyl esters of phenylalanine are treated with fumaryl chloride in organic solvent at 0°–60° C. to give chlorofumaryl phenylalanine alkyl esters which when hydrolyzed yield the fumaryl phenylalanine alkyl esters. Amination of these compounds yields aspartyl phenylalanine alkyl esters which are useful as artificial sweeteners.

Also of interest to the background of the present invention are J. Med. Chem. 18, No. 10, pp 1004–1010 (1975) disclosing the maleic amide of L-phenylalanine (Mal Phe); and the Japanese Kokai Patent No. 73 52,741 disclosing the maleic amide of the methyl ester of L-phenylalanine (Mal PM).

A need continues to exist in the art for improved methods for production of fumaryl compounds (e.g., fumaric acid and monoesters and amides thereof) from the corresponding maleyl compounds which are both efficient and economic and lend themselves to large scale commercial uses.

SUMMARY OF THE INVENTION

The present invention provides for the conversion of maleyl compounds to the corresponding fumaryl compounds with improved yields and efficiencies under conditions lending themselves to large scale production of the desired compounds. The process involves using substituted and unsubstituted thiourea compounds as inversion agents, preferably under anhydrous conditions and in the presence of hot acid, to isomerize "Z" isomer maleyl compounds to "E" isomer fumaryl compounds.

One aspect of the present invention provides processes for converting maleic acid according to the formula I to fumaric acid according to the formula Ia by subjecting maleic acid to an inversion agent consisting of certian substituted thioureas selected from the group consisting of ethylene thiourea and tetramethylthiourea.

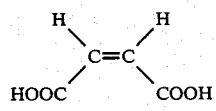

I

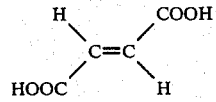

Ia

The second aspect of the present invention provides processes for the conversion of maleyl monoesters according to the formula II wherein R equals a C2–C7 alkyl, benzyl or phenyl, to the corresponding fumarate according to the formula IIa by subjecting the maleic compounds to the action of a thiourea or substituted thiourea inversion reagent.

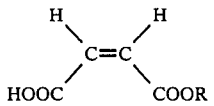
II

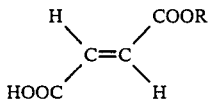
IIa

According to another aspect of the present invention, maleyl monoester compounds according to the formula II are converted to the corresponding fumaryl monoesters according to the formula IIa wherein R is a C2–C7 alkyl, benzyl, or phenyl by subjecting a substantially anhydrous acid solution of the maleyl compound to ethylene thiourea or tetramethyl thiourea. This process is distinguished from the process utilized in Spatz by the use of anhydrous acid conditions.

And in still another of its aspects, the present invention provides processes for converting maleyl monoamides according to the formula III to the corresponding fumaryl monoamides according to the formula IIIa.

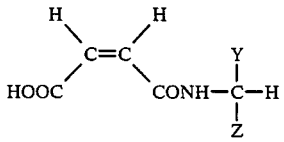
III

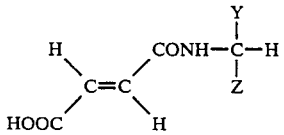
IIIa wherein Y is selected from the group consisting of hydrogen, carboxyl or lower alkyl of 1–8 carbon atoms, and Z is selected from the group consisting of hydrogen, hydroxy lower alkyl, thio lower alkyl, amino lower alkyl, amino nitrile lower alkyl, carboxy lower alkyl, amino oxy lower alkyl, nitrogen containing cyclic lower alkene, and hydroxy substituted benzyl or a $C_1$–$C_4$ lower alkyl ester thereof.

This process comprises subjecting the maleyl compound to a substituted or unsubstituted thiourea in an acid solution under anhydrous conditions at an elevated temperature.

Inversion agents useful in practice of the invention include those of formula IV, wherein $R^1$, $R^2$, $R^3$ and $R^4$ are the same or different and selected from the group consisting of hydrogen and a lower alkyl or wherein $R^1$ and $R^2$ form a cyclic ring and $R^3$ and $R^4$ equals hydrogen.

Preferred inversion agents of formula IV include thiourea wherein $R^1$, $R^2$, $R^3$ and $R^4$ equal hydrogen; tetramethylthiourea wherein $R^1$, $R^2$, $R^3$ and $R^4$ equal methyl; and ethylene thiourea wherein $R^1$ and $R^2$ equal $—CH_2—CH_2—$, and $R^3$ and $R^4$ equal hydrogen.

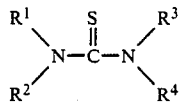
IV

In a preferred embodiment, maleyl phenylalanine or one of its lower alkyl esters is converted to the corresponding fumaryl form in high yield by treatment of the maleyl amide in anhydrous acid (e.g., methanesulfonic acid) at elevated temperatures (e.g., refluxing temperatures in the range of 20° to 120° C.) in the presence of thiourea, tetramethylthiourea or ethylene thiourea.

Other aspects and advantages of the present invention will be apparent upon consideration of the illustrative examples thereof as set forth in the following detailed description. The following examples are provided to further illustrate and define the teachings of the present invention and are in no way intended to limit its spirit or scope. Modifications in the materials and methods may be evident to those skilled in the art and are contemplated herein.

DETAILED DESCRIPTION OF THE INVENTION

The following illustrative examples relate to the preparation of fumaryl monoesters and monoamides from maleyl monoesters and monoamides.

As indicated in the examples, maleyl starting materials are readily prepared by reaction of maleic anhydride with a selected alcohol or amine. More particularly, Examples 1–3 relate to the preparation of monobenzyl maleate and its conversion to monobenzyl fumarate using thiourea, ethylene thiourea and tetramethylthiourea. Examples 4 through 8 relate to conversion of maleyl monoamides to their corresponding fumaryl compounds.

EXAMPLE 1

Preparation of Monobenzyl Fumarate Using Thiourea as a Catalyst

Maleic anhydride (55.9 g.) was added to 61.1 g. benzyl alcohol and the mixture heated at 60° C. for two hours at which time Nuclear Magnetic Resonance (NMR) revealed that about 72% of the anhydride had been converted to monobenzyl maleate. The temperature of the mixture was gradually heated to 90° C. over a 30 minute period and maintained at this temperature for one hour. NMR revealed that the reaction had reached chemical equilibrium with about 90–92% of the anhydride converted to monobenzyl maleate.

The oily product was cooled to room temperature and was dissolved in 400 ml. ethyl acetate. Water (150 ml.) was added, followed by gradual addition of 40.0 g. of potassium carbonate. The aqueous layer was removed from the organic layer and washed once with water. The combined aqueous extracts were washed with ethyl acetate and then acidified with the addition of 50 ml. of concentrated hydrochloric acid. The oil which separated was extracted into ethyl acetate and the organic layer was washed once with saturated sodium chloride solution. The organic layer was dried over anhydrous magnesium sulfate, filtered, and the ethyl acetate removed by distillation. The residual warm oil was dried under vacuum 1–2 mm Hg for 20–25 minutes. The oil then weighed 99.7 g (84.9% of theory)

and crystallized when seeded with solid monobenzyl maleate.

This product was isomerized to the fumarate by the following procedure. Monobenzyl maleate (99.7 g.) was dissolved in 485 ml. dry ethyl acetate and 1.84 g. of thiourea. Anhydrous methanesulfonic acid (4.6 ml) was then added. The mixture was heated under refluxing conditions for one hour and cooled to room temperature. The solution was washed with 100 ml. water and subsequently with 70 ml. saturated sodium chloride solution. This was then dried over anhydrous magnesium sulfate. The resulting solution was filtered and distilled under vacuum of 1-2 mm Hg leaving a solid residue which when dried at 70° C. for 15 hours afforded 96.0 g. (96.3% yield) of monobenzyl fumarate. The NMR spectrum showed the product to be free of monobenzyl maleate.

EXAMPLE 2

Preparation of Monobenzyl Fumarate Using Ethylenethiourea (2-Imidazolidinethione) as a Catalyst Maleic anhydride (55.9 g.) was added to 61.1 g. benzyl alcohol and the mixture was heated at 60° C. for two hours at which time NMR revealed that about 72% of the anhydride had been converted to monobenzyl maleate. The mixture was gradually heated to 90° C. over a 30 minute period and was maintained at this temperature for one hour. NMR revealed that the reaction had reached chemical equilibrium with about 90-92% of the anhydride converted to monobenzyl maleate.

The oily product was cooled to room temperature and dissolved in 400 ml. ethyl acetate. Water (150 ml.) was added, followed by gradual addition of 40.0 g. of potassium carbonate. The aqueous layer was removed from the organic layer and washed once with water. The combined aqueous extracts were washed with ethyl acetate and acidified by the addition of 50 ml. of concentrated hydrochloric acid. The oil which separated was extracted into ethyl acetate and the organic layer was washed once with saturated sodium chloride solution. The organic layer was dried over anhydrous magnesium sulfate, filtered and the ethyl acetate removed by distillation. The residual warm oil was dried under vacuum 1–2 mm Hg for 20–25 minutes. The oil then weighed 99.7 g. (84.9% of theory) and crystallized when seeded with solid monobenzyl maleate.

This compound was isomerized to the fumarate using the following procedure. Monobenzyl maleate (2.06 g.) was dissolved in 20.6 ml. dry ethyl acetate and 0.051 g. of 2-imidazolidinethione. Methanesulfonic acid (0.073 ml) was added to the solution and the mixture was heated at reflux for one hour, cooled to 25° C., washed with 25 ml. water, and dried over anhydrous sodium sulfate. The resulting solution was filtered, the solvent distilled, and the solid residue dried at 0.1 mm Hg pressure. The NMR spectrum in $CDCl_3$ showed the resulting material to be entirely monobenzyl fumarate.

EXAMPLE 3

Preparation of Monobenzyl Fumarate Using Tetramethylthiourea as a Catalyst

Maleic anhydride (55.9 g.) was added to 61.1 g. benzyl alcohol and the mixture heated at 60° C. for two hours at which time NMR revealed that about 72% of the anhydride had been converted to monobenzyl maleate. The mixture was gradually heated to 90° C. over a 30 minute period and maintained at this temperature for one hour. NMR revealed that the reaction had reached chemical equilibrium with about 90–92% of the anhydride converted to monobenzyl maleate.

The oily product was cooled to room temperature and dissolved in 400 ml. ethyl acetate. Water (150 ml.) was added, followed by gradual addition of 40.0 g. potassium carbonate. The aqueous layer was removed from the organic layer and washed once with water. The combined aqueous extracts were washed with ethyl acetate and then acidified by addition of 50 ml. of concentrated hydrochloric acid. The oil which separated was extracted into ethyl acetate and the organic layer was washed once with saturated sodium chloride solution. The organic layer was dried over anhydrous magnesium sulfate, filtered and the ethyl acetate was removed by distillation. The residual warm oil was dried under a vacuum 1–2 mm Hg for 20–25 minutes. The oil then weighed 99.7 g. (84.9% of theory) and crystallized when seeded with solid monobenzyl maleate.

This compound was isomerized to the fumarate by the following procedure. Monobenzyl maleate (2.06 g.) was dissolved in 20.6 ml. dry ethyl acetate and 0.066 g. of tetramethyl thiourea. Methanesulfonic acid (0.073 ml) was added to the solution, the mixture heated at reflux for one hour, cooled to 25° C., washed with 25 ml. water, and dried over anhydrous sodium sulfate. The resulting solution was filtered, the solvent distilled, and the solid residue dried at a vacuum of 0.1 mm Hg. The NMR in $CDCl_3$ showed the material to be entirely monobenzyl fumarate.

EXAMPLE 4

Preparation of (E)-N-(3-Carboxy-1-oxo-2-propenyl)-L-phenylalanine Methyl Ester Powdered maleic anhydride (98.0 g.) was added to a solution of 179.2 g. L-phenylalanine methyl ester dissolved in 1.77 l. dry ethyl acetate which was stirred well. The temperature of the mixture rose from 28° C. to 38° C. as the anhydride dissolved. The resulting solution of (Z)-N-(3-carboxy-1-oxo-2 propenyl)-L-phenylalanine methyl ester was allowed to stand overnight.

This compound was then isomerized to the fumaryl ester by the following procedure. Thiourea (3.845 g.) and 7.28 ml. anhydrous methanesulfonic acid were added to the ethyl acetate solution of (Z)-N-(3-Carboxy-1-oxo-2-propenyl)-L-phenylalanine methyl ester and stirred at reflux for 90 minutes. The solution was cooled to 25° C. and washed three times with equal portions of water. The aqueous extracts were backwashed with 500 ml. ethyl acetate and the combined organic extracts were dried over anhydrous sodium sulfate. The solution was filtered and the solvent distilled under vacuum of 1-2 mm Hg. The residual solid was dried to constant weight in air to afford 262.5 g. (94.7% of theory) of (E)-N-(3-carboxy-1-oxo-2-propenyl)-L-phenylalanine methyl ester. The NMR established that no (Z) isomer was present in the product.

EXAMPLE 5

Preparation of (E)-4-(Methylamino-4-oxo-2-butenoic Acid

Maleic anhydride (98.06 g.) was mixed in a 2.0 l. flask with 74.27 g. methylamine hydrochloride and 1.0 l. glacial acetic acid. The resulting clear solution was stirred and 90.23 g. anhydrous sodium acetate added. The mixture became turbid and the temperature rose from 20° to 31° C. After one hour, most of the acetic acid was distilled under vacuum of 1-2 mm Hg at about 40° C. The residual thick paste was diluted with 500 ml. water and the mixture was then stirred for 15 minutes, cooled to 20° C. and the solid collected on a filter. This residue was rinsed with about 50 ml. of water, and dried to constant weight in air. The yield of (Z)-(4-methylamino)-4-oxo-2-butenoic acid was 99.6 g. (77.1% of theory).

The resulting compound was isomerized to the fumaryl monoamide by the following procedure. (Z)-4-(Methylamino)4-oxo-2--butenoic acid (99.0 g.) was dissolved in 990 ml. dry ethyl acetate, 2.92 g. thiourea and 4.98 ml. anhydrous methanesulfonic acid. The mixture was stirred at reflux for 90 minutes and cooled to 25° C. After the addition of 50 ml. water, the suspended solid material was collected on a filter, rinsed with ethyl acetate, and air-dried to afford 64.0 g. of (E)-4-(methylamino)-4-oxo-2-butenoic acid. An additional 4.9 g. of product was obtained by evaporation of the ethyl acetate extract and an additional 7.4 g. was obtained by extraction of the aqueous filtrate with two 500 ml. portions of ethyl acetate. The total yield of product was 76.3 g. (77.1% of theory). The NMR spectrum in $d_6$-dimethylsulfoxide showed the material to be free of Z-isomer.

EXAMPLE 6

Preparation of (E)-N-(3-Carboxy-1-oxo-2-propenyl)-glycine Methyl Ester

Maleic anhydride (98.06 g.) and 125.6 g. glycine methyl ester hydrochloride were dissolved in 1.0 1. glacial acetic acid. Sodium acetate (82.0 g.) was added and the mixture was stirred for one hour. Most of the acetic acid was distilled at 35°–40° C. under vacuum of 1–2 mm Hg and the residual thick paste was treated with water. The mixture was stirred for an hour, the solid product collected on a filter, was rinsed with 200 ml. water and dried in air to afford 114.6 g. of (Z)-N-(3-carboxy-1-oxo-2-propenyl)-glycine methyl ester. An additional 10.4 g. of this compound was isolated by extraction of the aqueous filtrate with two 500 ml. portions of ethyl acetate for a total yield of 125.0 g. (66.7% of theory).

This compound was isomerized to the fumaryl monoamide ester using the following procedure. (Z)-N-(3-Carboxy-1-oxo-2-propenyl)-glycine methyl ester (113.6 g.) was mixed with 1.136 1. dry ethyl acetate, 2.31 g. thiourea, and 3.94 ml. methanesulfonic acid. The mixture was stirred at reflux temperature for one hour and cooled to 15° C. The suspended solid was collected on a filter and rinsed with 100 ml. ethyl acetate and 500 ml. water and dried in air to afford 104.8 g. (92.3% of theory) of (E)-N-(3-carboxy-1-oxo-2-propenyl)-glycine methyl ester. The NMR in $d_6$-dimethysulfoxide showed the product to be free of the Z-isomer.

EXAMPLE 7

Preparation of (E)-N-(3-Carboxy-1-oxo-2-propenyl)-L-alanine Methyl Ester

Maleic anhydride (35.1 g.) and 50.0 g. L-alanine methyl ester hydrochloride were mixed in 358 ml. glacial acetic acid followed by the addition of 29.4 g. anhydrous sodium acetate. The temperature of the mixture rose from 20° to 30° C. as the reaction occurred. After the mixture had been stirred for one hour, the acetic acid was distilled under vacuum at 35-40° C. and the residual paste mixed with 180 ml. water. The resulting solution was cooled to 15° C., whereupon the mixture became solid as the product crystallized. The solid mass was broken up with a spatula, collected on a filter, rinsed with 25 ml. water and air dried to a constant weight to afford 67.6 g. (93.9% of theory) of (Z)-N-(3-carboxy-1-oxo-2-propenyl)-L-alanine methyl ester.

This compound was isomerized to the fumaryl amide ester by the following procedure. (Z)-N-(3-Carboxy-1-oxo-2-propenyl) -L-alanine methyl ester (67.5 g.) was mixed with 1.28 g. thiourea and 2.18 ml. anhydrous methanesulfonic acid in 675 ml. dry ethyl acetate. The mixture was stirred at reflux for one hour and cooled to 25° C. After addition of 500 ml. water, the organic layer was separated and dried over anhydrous sodium sulphate. The solution was filtered and the solvent distilled under vacuum of 1–2 mm Hg leaving a solid residue that was dried to constant weight affording 50.1 g (74.2% yield) of the (E)N-(3-carboxy-1-oxo-2-propenyl)-L-alanine methyl ester. The NMR in $d_6$-dimethyl sulfoxide showed the product to be free of the Z-isomer.

EXAMPLE 8

Preparation of (E)-N-(3-Carboxy-1-oxo-2-propenyl) -L-phenylalanine

L-Phenylalanine (165.0 g.) and 98.0 g. maleic anhydride were mixed in 500 ml. dry tetrahydrofuran (THF). The mixture was stirred at reflux temperature for one hour, the solid largely dissolving during this time. The mixture was cooled to room temperature and filtered to remove a small amount of insoluble material. THF was distilled from the filtrate under a vacuum of 1–2 mm Hg to leave a solid residue. The solid was stirred with 500 ml. acetone and the solvent distilled under a vacuum of 1–2 mm Hg. The acetone treatment was repeated. The residual solid was ground in a mortar and dried to a constant weight at a pressure of about 0.1 mm Hg to yield 262.9 g. (99.9% of theory) of (Z)-N-(3-carboxy-1-oxo-2-propenyl)-L-phenylalanine.

This compound was isomerized to the fumaryl monoamide using the following procedure. (Z)-N-(3-Carboxy-1-oxo-2-propenyl) -L-phenylalanine (260.0 g.) was mixed with 2.6 1. dry ethyl acetate, 3.80 g. thiourea and 7.19 ml. methanesulfonic acid. The mixture was stirred at reflux temperature for one hour and cooled to 25° C. The crystalline precipitate was collected on a filter, rinsed with 500 ml. ethyl acetate, and dried in air at room temperature to constant weight. The yield of (E)-N-(3-carboxy-1-oxo-2-propenyl)-L-phenylalanine was 226.5 g. (87.1% of theory). The NMR indicated that no Z-isomer was present.

In the present invention the thiourea compound is present in a concentration from about 4 molar percent to about 10 molar percent of said maleyl compound, and preferably is present in a concentration from about 4 molar percent to about 6 molar percent of said maleyl compound, and most preferably is present at a concentration of about 5 molar percent.

The process is conducted at an elevated temperature of from about 20° C. to about 120° C. and more preferably from about 60° C. to 82° C. The acids used in carrying out the isomerization reaction are preferably those selected from the sulphonic family although hydrochloric acid and other anyhydrous acids with a $pK_a$ value less than or equal to 1.0 may be suitable.

Ethylene thiourea, tetramethylthiourea and thiourea are presently preferred as inversion reagents. Solvents well utilized are acetonitrile, tetrahydrofuran, and preferably, ethyl acetate.

This process is especially useful in the preparation of intermediates for dipeptide sweeteners and according to one embodiment may be utilized in the production of the dipeptide sweetener aspartame. Specifically, when the reaction product of maleic anhydride and L-phenylalanine is treated under refluxing, anhydrous conditions in the presence of strong acid and thiourea, fumaryl-L-phenylalanine is obtained in nearly pure yield. Enzymatic or chemical amination of fumaryl-L-phenylalanine results in L-aspartyl L-phenylalanine. Methylation of the phenylalanine moiety of that compound yields L-aspartyl L-phenylalanine methyl ester, or aspartame.

Other artificial sweeteners which may be synthesized using this process are those resulting from the isomeric conversion and subsequent amination of maleyl-L-phenylalanine ethyl or propyl ester; methyl 2,5-dimethylcyclopentyl maleate; methyl 2,6-dimethylcyclohexyl maleate; ethyl 2,5-dimethylcyclopentyl maleate; ethyl 2,6-dimethylcyclohexyl maleate, methyl-fenchyl maleate; ethyl-fenchyl maleate; (S)-a-phenethyl maleyl amide; (S)-2,4-dimethylpentyl maleyl amide; (S)-1-phenyl-2-propyl maleyl amide; maleyl (S)-tert-butyl-cystein methyl ester; maleyl methionine methyl ester; and maleyl tyrosine methyl ester.

I claim:

1. A process for converting a maleyl monoester compound according to formla II to the coresponding fumaryl monoester compound of formula IIa;

wherein R is a $C_2$–$C_7$ alkyl, benzyl or phenyl,

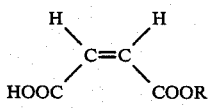

II

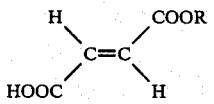

IIa said process comprising treating the maleyl compound with a substituted or unsbstituted thiourea inversion agent in an acid solution under anhydrous conditions.

2. A process for converting a maleyl monoamide compound according to formula III to the corresponding fumarly monomide compound according to formula IIIa;

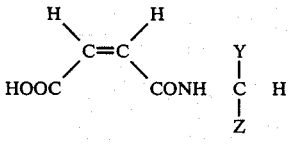

III

-continued

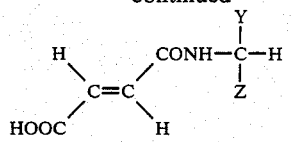

IIIa wherein: Y is selected from the group consisting of hydrogen, carboxyl or lower alkyl of 1–8 carbon atoms; and z is selected from the group consisting of hydrogen, hydroxy lower alkyl, thio lower alkyl, amino lower alkyl, amino nitrile lower alkyl, carboxy lower alkyl, amino oxy lower alkyl, a nitrogen containing cyclic lower alkene, and a hydroxy substituted benzyl radical, or a $C_1$–$C_4$ alkyl-ester thereof, said process comprising treating the maleyl compound with substituted or unsubstituted thiourea in an acid solution under anhydrous conditions.

3. A process according to claims 1 or 2 wherein the inversion agent is a compound of the formula IV;

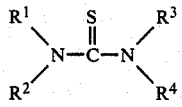

IV wherein:

$R^1$, $R^2$, $R^3$, and $R^4$ are the same or different and selected from the group consisting of hydrogen and a lower alkyl;

or $R^1$ and $R^2$ form a cyclic ring and $R^3$ and $R^4$ equal hydrogen.

4. A process according to claim 3 wherein the inversion agent is selected from the group consisting of thiourea, tetramethylthiourea and ethylene thiourea.

5. A process according to claim 1 or 2 wherein said inversion agent is present in a concentration from about 0.5 molar percent to about 10 molar percent of said maleyl compound.

6. A process according to claim 1 or 2, wherein said inversion agent is present in a concentration from about 4 molar percent to about 6 molar percent of said maleyl compound.

7. A process according to claims 1 or 2 wherein said acid is selected from the group comprising anhydrous acids with a pKa value less than or equal to 1.0.

8. A process according to claim 8 wherein said acid is selected from the group comprising anhydrous sulphonic acids.

9. The process according to claim 8 wherein said conversion is carried out at a temperature in a range of from about 20° C. to about 120° C.

10. The process according to claim 9 wherein said temperature range is approximately 60° C. to 82° C.

11. A process for the conversion of maleyl phenylalanine or a lower alkyl ester thereof to fumaryl phenylalanine or a lower alkyl ester thereof, said process comprising: treating an anhydrous methanesulfonic acid solution of the maleyl compound with an inversion agent selected from the group consisting of thiourea, ethylene thiourea and tetramethylthiourea in a concentration of from 0.5 to 10 molar percent and at a temperature of from about 60° C. to about 82° C.

* * * * *